United States Patent [19]

Harada

[11] Patent Number: 5,639,912
[45] Date of Patent: Jun. 17, 1997

[54] DIANILINOGLUTACONDIALDEHYDE COMPOUND AND PROCESS FOR THE PREPARATION THEREOF

[75] Inventor: Toru Harada, Kanagawa, Japan

[73] Assignee: Fuji Photo Film co., Ltd., Kanagawa, Japan

[21] Appl. No.: 627,131

[22] Filed: Apr. 3, 1996

[30] Foreign Application Priority Data

Apr. 17, 1995 [JP] Japan .................................. 7-090717

[51] Int. Cl.$^6$ ............... C07C 249/02; C07C 251/24; C07C 251/30; A61K 31/135
[52] U.S. Cl. ................ 564/270; 564/272; 564/276; 564/277
[58] Field of Search .................... 514/255, 641; 8/654, 655; 564/270, 272, 276, 277

[56] References Cited

U.S. PATENT DOCUMENTS

| | | | |
|---|---|---|---|
| 3,482,978 | 12/1969 | Fumia et al. | 96/84 |
| 3,552,974 | 1/1971 | Jeffreys et al. | 96/129 |

OTHER PUBLICATIONS

Organic Synthesis, Collective vol. 4, pp. 464–466, (1963).

*Primary Examiner*—Peter O'Sullivan
*Attorney, Agent, or Firm*—Birch, Stewart, Kolasch & Birch, LLP

[57] ABSTRACT

A dianilinoglutacondialdehyde compound is described, which is represented by the following formula (Ia) or (Ib):

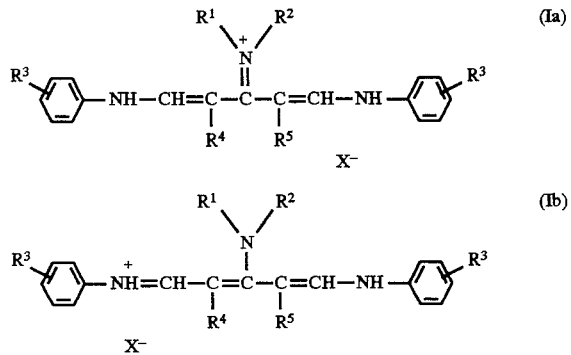

wherein $R^1$ and $R^2$ each represents an alkyl group or an aryl group and may be connected to each other; $R^3$ represents a hydrogen atom, an alkyl group, an alkoxy group or a halogen atom; $R^4$ and $R^5$ each represents a hydrogen atom or a non-metallic atom which is required to be connected to each other to form a 5- or 6-membered ring; and $X^-$ represents $BF_4^-$, $SbF_6^-$ or $PF_6^-$. A process for the preparation of the compound as described above is also described.

4 Claims, No Drawings

DIANILINOGLUTACONDIALDEHYDE COMPOUND AND PROCESS FOR THE PREPARATION THEREOF

FIELD OF THE INVENTION

The present invention relates to a dianilinoglutacondialdehyde compound useful as an intermediate of cyanine compound and a process for the preparation thereof. The compound of the present invention can be used as a dye, a photographic dye, a photographic sensitizing dye, a filter dye, an ink, a recording compound for optical data recording medium, a dye for living specimen such as a cell, a medicine or an intermediate thereof.

BACKGROUND OF THE INVENTION

A dianilinoglutacondialdehyde compound having an amino group in the meso-position contains a $ClO_4^-$ ion as a paired ion as described in U.S. Pat. Nos. 3,482,978 and 3,552,974. A compound containing $ClO_4^-$ is explosive and thus is not suitable for production. Such a compound has been synthesized from ethyl N-phenylformimidate. Ethyl N-phenylformimidate is synthesized by a method described in "ORGANIC SYNTHESES", Collective Volume 4, pp. 464–466. However, this synthesis method requires distillation.

SUMMARY OF THE INVENTION

It is therefore an object of the present invention to provide a non-explosive dianilinoglutacondialdehyde compound containing an amino group in the meso-position. It is another object of the present invention to provide a process for the easy preparation of such a useful intermediate at a low cost.

The foregoing objects of the present invention can be accomplished with a dianilinoglutacondialdehyde compound represented by the following formula (Ia) or (Ib):

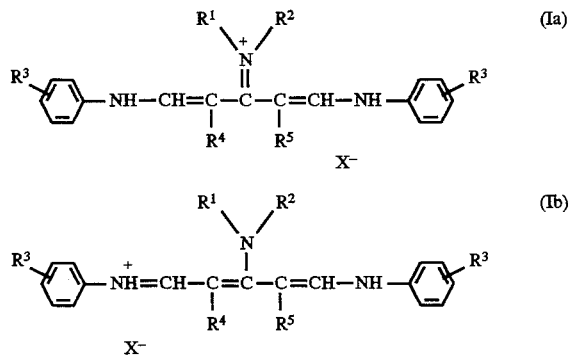

wherein $R^1$ and $R^2$ each represents an alkyl group or an aryl group and may be connected to each other; $R^3$ represents a hydrogen atom, an alkyl group, an alkoxy group or a halogen atom; $R^4$ and $R^5$ each represents a hydrogen atom or a non-metallic atom which is required to be connected to each other to form a 5- or 6-membered ring; and $X^-$ represents $BF_4^-$, $SbF_6^-$ or $PF_6^-$.

DETAILED DESCRIPTION OF THE INVENTION

The formula (Ia) or-(Ib) will be further described hereinafter. The alkyl group represented by $R^1$, $R^2$ or $R^3$ may be substituted by a hydroxyl group, a halogen atom (Cl, F, Br) or the like. The alkl group is preferably an unsubstituted alkyl group such as a methyl group, an ethyl group, a propyl group and a butyl group.

The aryl group represented by $R^1$ or $R^2$ is a phenyl or naphthyl group which may be substituted by a methyl group, a methoxy group, a halogen atom (Cl, Br, F), a carboxyl group, a methoxycarbonyl group or a hydroxyl group. The aryl group is preferably an unsubstituted phenyl group.

Examples of the ring formed by the connection of $R^1$ to $R^2$ include piperidine, piperazine, indoline, morpholine, and pyrrolidine.

Preferably, at least one of $R^1$ and $R^2$ is a phenyl group.

Examples of the alkoxy group represented by $R^3$ include a methoxy group and an ethoxy group. Examples of the halogen atom represented by $R^3$ include Cl, Br, and F. $R^3$ is preferably a hydrogen atom.

Examples of the 5- or 6-membered ring formed by $R^4$ and $R^5$ include heterocyclic hydrocarbon and carbocyclic hydrocarbon. The 5- or 6-membered ring is preferably a carbocyclic hydrocarbon. Examples of the carbocyclic hydrocarbon represented by the formula (Ia) include cyclopentane and cyclohexane. (Examples of the carbocyclic hydrocarbon represented by the formula (Ib) include cyclopentene and cyclohexene. This can apply hereinafter.) Such a ring may be substituted by a methyl group, a t-butyl group or a phenyl group. It is preferred that $R^4$ and $R^5$ be connected to each other to form a 5-membered carbocyclic hydrocarbon.

Preferred among the paired ions represented by $X^-$ is $BF_4^-$.

More preferably, at least one of $R^1$ and $R^2$ is a phenyl group. $R^3$ is a hydrogen atom. $R^4$ and $R^5$ together form a 5-membered carbocyclic hydrocarbon. $X^-$ is $BF_4^-$.

The foregoing objects of the present invention can also be accomplished by a preparation process of the dianilinoglutacondialdehyde compound represented by the formula (Ia) or (Ib) which comprises the reaction of an orthoester, an aniline compound and an iminium cation represented by the following formula (II) in the presence of an acid. The preparation process of the present invention can be represented by the following reaction formula:

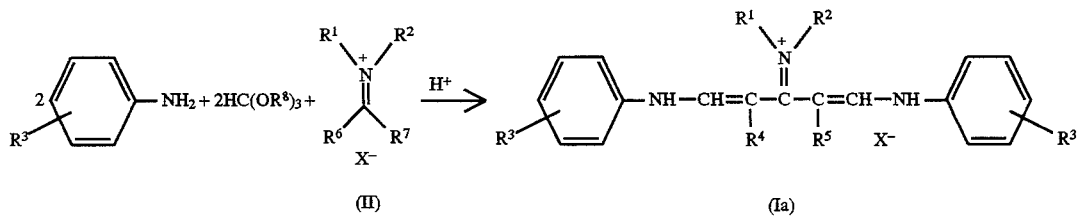

or

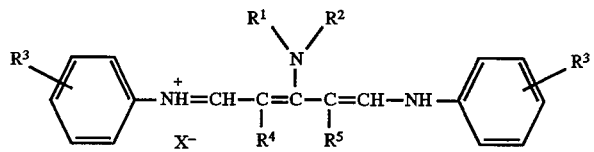

(Ib)

wherein $R^1$ and $R^2$ each represents an alkyl group or an aryl group and may be connected to each other; $R^6$ and $R^7$ each represents a methyl group or a non-metallic atom which is required to be connected to each other to form a 5- or 6-membered ring; $R^3$ represents a hydrogen atom, an alkyl group, an alkoxy group or a halogen atom; $R^8$ represents a methyl group or an ethyl group; $R^4$ and $R^5$ each represents a hydrogen atom or a non-metallic atom which is required to be connected to each other to form a 5- or 6-membered ring; and $X^-$ represents $BF_4^-$, $SbF_6^-$ or $PF_6^-$.

The various substituents will be further described hereinafter. $R^1$, $R^2$, $R^3$, $R^4$, $R^5$ and $X^-$ are defined above. The formation of a 5- or 6-membered ring by $R^6$ and $R^7$ has the same meaning as that by $R^4$ and $R^5$.

More preferably, at least one of $R^1$ and $R^2$ is a phenyl group. $R^3$ is a hydrogen atom. $R^6$ and $R^7$, or $R^4$ and $R^5$ together form a 5-membered carbocyclic hydrocarbon. $X^-$ is $BF_4^-$.

The foregoing reaction is preferably effected by the reaction of an aniline compound, an orthoester and an iminium cation in a solvent (e.g., alcohol, acetonitrile, N,N-dimethylformamide) or free of solvent in the presence of an acid (e.g., sulfuric acid, hydrochloric acid, acetic acid) at a temperature of from 0° C. to 150° C., more preferably from 50° C. to 120° C. The solvent may be used in the form of a mixture of two or more thereof.

In a still preferred embodiment of the reaction process, an aniline compound and an orthoester react free of solvent while resulting alcohol is being distilled off at a temperature of 80° C. to 120° C. Subsequently, a solvent such as acetonitrile and alcohol and an iminium cation are added to the reaction system which is then allowed to undergo reaction at a temperature of from 60° C. to 100° C. The solvent may be used in the form of a mixture thereof.

Alternatively, $HBF_4$, $HPF_6$, $HSbF_6$ or the like may be added dropwise to a mixture of an amine compound represented by $R^1R^2NH$, a ketone compound represented by $R^6$—C(=O)—$R^7$ (in which $R^1$, $R^2$, $R^6$ and $R^7$ are as defined above) and a solvent such as isopropyl alcohol, ethyl alcohol, acetonitrile and methyl alcohol to synthesize an iminium cation which is then allowed to undergo the foregoing reaction in one pot. The solvent may be used in the form of a mixture of two or more thereof.

The foregoing objects of the present invention can further be accomplished by the reaction of an N,N-diphenylformamidine compound represented by the formula (III) with an iminium cation represented by the formula (II). The preparation process can be represented by the following reaction formula:

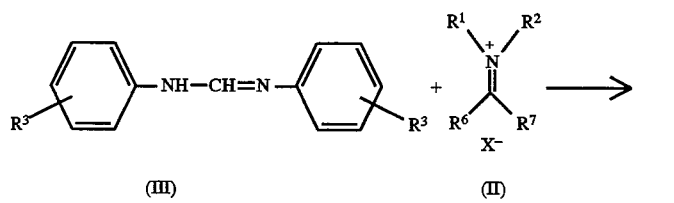

(III)  (II)

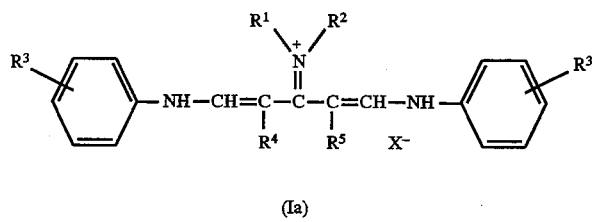

(Ia)

or

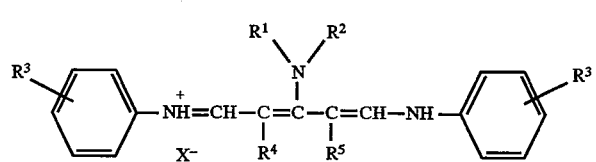

(Ib)

wherein $R^3$ represents a hydrogen atom, an alkyl group, an alkoxy group or a halogen atom; $R^1$ and $R^2$ each represents an alkyl group or an aryl group and may be connected to each other; $R^6$ and $R^7$ each represents a methyl group or a non-metallic atom which is required to be connected to each other to form a 5- or 6-membered ring; $R^4$ and $R^5$ each represents a hydrogen atom or a non-metallic atom which is required to be connected to each other to form a 5- or 6-membered ring; and $X^-$ represents $BF_4^-$, $SbF_6^-$ or $PF_6^-$.

These substituents have the same meaning as mentioned above. More preferably, at least one of $R^1$ and $R^2$ is a phenyl group. $R^3$ is a hydrogen atom: $R^6$ and $R^7$, or $R^4$ and $R^5$ together form a 5-membered carbocyclic hydrocarbon. $X^-$ is $BF_4^-$.

The foregoing reaction is preferably effected by the reaction of an N,N-diphenylformamidine compound with an iminium cation in a solvent (e.g., alcohol, acetonitrile, N,N-dimethylformamide) or free of solvent at a temperature of from 0° C. to 150° C., preferably from 50° C. to 100° C., optionally in the presence of acetic anhydride. The solvent may be used in the form of a mixture of two or more thereof.

Specific examples of the compound of the present invention will be given below. These compounds are represented by formulae based on (Ia) for convenience.

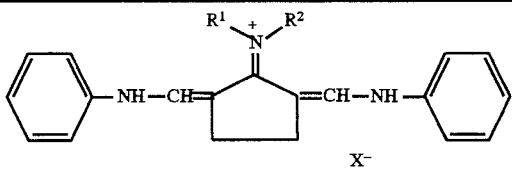

-continued

| 10 | [structure: piperazinium with =N⁺ and N—CO₂C₂H₅] |

[structure: diphenyl-N⁺ cyclopentane with two =CH—NH—C₆H₄—R¹¹ arms, BF₄⁻]

| Compound No. | R¹¹ |
|---|---|
| 11 | CH₃— |
| 12 | Cl— |
| 13 | CH₃O— |

[structure: diphenyl-N⁺ cyclohexane with two =CH—NH—C₆H₅ arms and R¹² substituent, BF₄⁻]

| Compound No. | R¹² |
|---|---|
| 14 | H— |
| 15 | CH₃— |
| 16 | [phenyl structure] |

Compound No. 17

[structure: Ph₂N⁺=C(—CH=CH—NH—C₆H₅)₂, BF₄⁻]

The present invention will be further described in the following examples.

EXAMPLE 1

(Synthesis of 1-cyclopentylidenediphenylaminium tetrafluoroborate)

A solution of 507 g of diphenylamine and 302.8 g of cyclopentanone dissolved in 800 ml of isopropyl alcohol was cooled to a temperature of 5° C. To the solution was then added dropwise 940.8 g of 42% HBF₄ solution dissolved in isopropyl alcohol at a temperature of not higher than 20° C. in 30 minutes. After the completion of the dropwise addition, the reaction mixture was stirred for 1 hour as it was. The resulting crystal was then separated by filtration.

Yield: 875 g (90.3%); m.p.: 205 °–207° C.

(Synthesis of Compound 1)

A solution of 277.8 g of ethyl N-phenylformimidate, 117.5 g of aniline and 1 g of concentrated sulfuric acid was stirred at an external temperature of 120° C. while the resulting ethyl alcohol was being distilled off for 2 hours. To the reaction system were then added 161.4 g of 1-cyclopentylidenediphenylaminium tetrafluoroborate and 100 ml of acetonitrile. The reaction mixture was then heated under reflux for 30 minutes. The reaction system was then allowed to cool to room temperature. The resulting crystal was then separated by filtration to obtain Compound 1.

Yield: 212.7 g (80.4%); m.p.: not lower than 250° C.;
λmax: 515.0 (MeOH)

(Calorimetry by DSC)

Compound 1 was measured for calorific value by DSC. A comparative compound was measured at the same time.

Compound 1—23 cal/g

Comparative Compound a—226 cal/g

Comparative Compound a

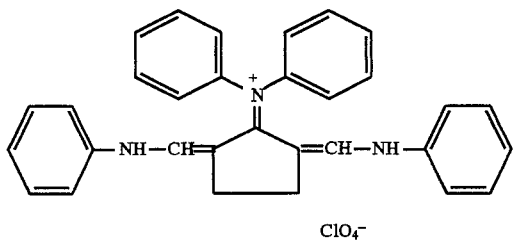

DSC stands for differential scanning calorimetry. It is further described in Seishi Tanaka & Yoshio Iida, "Kikibunseki (Instrumental Analysis)", Shokabo, page 312. The results show that the compound of the present invention exhibits a less calorific value than the comparative compound a and thus is non-explosive.

EXAMPLES 2 TO 17

The reaction procedure of Example 1 was followed to synthesize Compounds 2 to 17. The results of λmax of these compounds are set forth in Table 1. All these compounds exhibited a calorific value by DSC of not more than 30 cal/g and thus presented no explosion problem.

TABLE 1

| Compound No. | λmax/MeOH |
|---|---|
| 2 | 508.5 nm |
| 3 | 528.5 nm |
| 4 | 508.5 nm |
| 5 | 486.0 nm |
| 6 | 513.0 nm |
| 7 | 515.0 nm |
| 8 | 465.0 nm |
| 9 | 450.0 nm |
| 10 | 477.0 nm |
| 11 | 516.0 nm |
| 12 | 506.5 nm |
| 13 | 519.5 nm |
| 14 | 505.0 nm |
| 15 | 507.0 nm |
| 16 | 508.0 nm |
| 17 | 503.0 nm |

EXAMPLE 18

(Synthesis of Compound 1)

A mixture of 3.2 g of 1-cyclopentylidenediphenylaminium tetrafluoroborate, 4.9 g of N,N-diphenylformamidine, 5 ml of acetonitrile and 1 ml of acetic anhydride was heated under reflux for 2 hours. The resulting crystal was separated by filtration.

Yield: 2.3 g (43.5%); m.p.: not lower than 250° C.

It was thus found that the compound of the present invention is non-explosive and thus is suitable for production. Further, the preparation process of the present invention requires no distillation and thus can be operated at a reduced number of steps and a low cost.

While the invention has been described in detail and with reference to specific embodiments thereof, it will be apparent to one skilled in the art that various changes and modifications can be made therein without departing from the spirit and scope thereof.

What is claimed is:

1. A dianilinoglutacondialdehyde compound represented by the following formula (Ia) or (Ib):

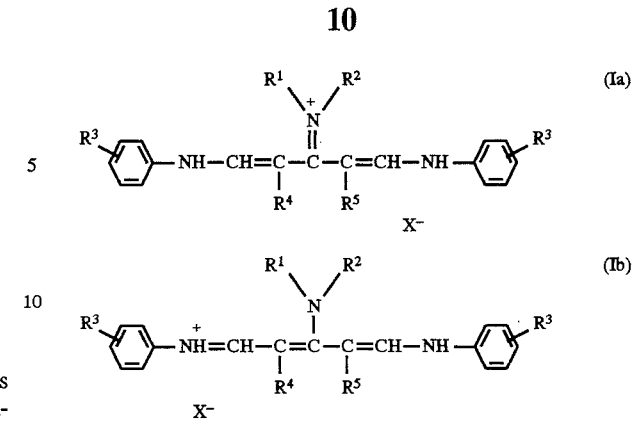

wherein $R^1$ and $R^2$ each represents an alkyl group or an aryl group and may be connected to each other; $R^3$ represents a hydrogen atom, an alkyl group, an alkoxy group or a halogen atom; $R^4$ and $R^5$ each represents a hydrogen atom or a non-metallic atom which is required to be connected to each other to form a 5- or 6-membered ring; and $X^-$ represents $BF_4^-$, $SbF_6^-$ or $PF_6^-$.

2. A process for the preparation of a dianilinoglutacondialdehyde compound represented by the following formula (Ia) or (Ib), which comprises the reaction of an orthoester, an aniline compound and an iminium cation represented by the following formula (II) in the presence of an acid:

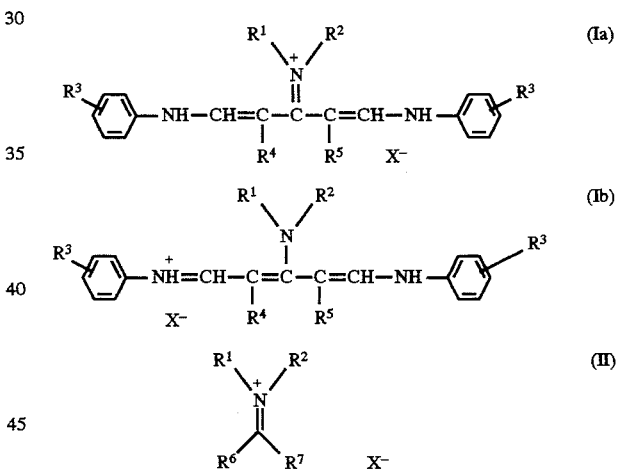

wherein $R^1$ and $R^2$ each represents an alkyl group or an aryl group and may be connected to each other; $R^3$ represents a hydrogen atom, an alkyl group, an alkoxy group or a halogen atom; $R^4$ and $R^5$ each represents a hydrogen atom or a non-metallic atom which is required to be connected to each other to form a 5- or 6-membered ring; $R^6$ and $R^7$ each represents a methyl group or a non-metallic atom which is required to be connected to each other to form a 5- or 6-membered ring; and $X^-$ represents $BF_4^-$, $SbF_6^-$ or $PF_6^-$.

3. The process for the preparation of the dianilinoglutacondialdehyde compound according to claim 2, wherein the aniline compound and the orthoester react free of solvent while resulting alcohol is being distilled off at a temperature of 80° C. to 120° C. and the iminium cation is added to the reaction system, which is then allowed to undergo reaction at a temperature of from 60° C. to 100° C.

4. A process for the preparation of a dianilinoglutacondialdehyde compound represented by the following formula (Ia) or (Ib), which comprises the reaction of an N,N-diphenylformaldehyde compound represented by the following formula (III) with an iminium cation represented by the following formula (II):

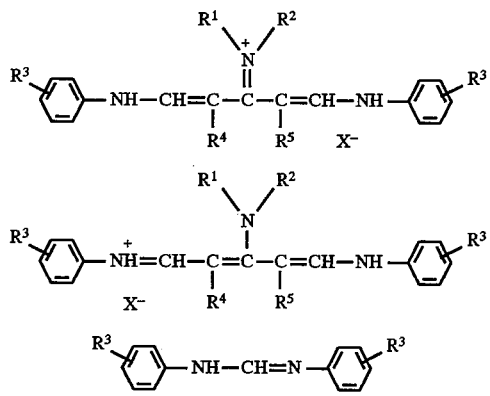

wherein $R^1$ and $R^2$ each represents an alkyl group or an aryl group and may be connected to each other; $R^3$ represents a hydrogen atom, an alkyl group, an alkoxy group or a halogen atom; $R^4$ and $R^5$ each represents a hydrogen atom or a non-metallic atom which is required to be connected to each other to form a 5- or 6-membered ring; $R^6$ and $R^7$ each represents a methyl group or a non-metallic atom which is required to be connected to each other to form a 5- or 6-membered ring; and $X^-$ represents $BF_4^-$, $SbF_6^-$ or $PF_6^-$.

* * * * *